(12) United States Patent
Yonehara et al.

(10) Patent No.: US 7,838,304 B2
(45) Date of Patent: Nov. 23, 2010

(54) LIQUID REAGENT OF COLOR FORMER AND METHOD OF STABILIZING THE SAME

(75) Inventors: Satoshi Yonehara, Kyoto (JP); Norio Inamura, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 35 days.

(21) Appl. No.: 12/087,833

(22) PCT Filed: Jan. 18, 2007

(86) PCT No.: PCT/JP2007/050697

§ 371 (c)(1),
(2), (4) Date: Jul. 16, 2008

(87) PCT Pub. No.: WO2007/083703

PCT Pub. Date: Jul. 26, 2007

(65) Prior Publication Data

US 2009/0053823 A1  Feb. 26, 2009

(30) Foreign Application Priority Data

Jan. 18, 2006  (JP) .............................. 2006-010372

(51) Int. Cl.
*G01N 21/78*  (2006.01)

(52) U.S. Cl. ........................ 436/176; 436/8; 436/164; 436/166; 436/174; 436/106; 436/111; 252/408.1; 422/61

(58) Field of Classification Search .................... 436/8, 436/164, 166, 174, 176, 106, 111; 252/408.1; 422/61

See application file for complete search history.

(56) References Cited

U.S. PATENT DOCUMENTS

| 4,290,769 A | 9/1981 | Liao et al. |
|---|---|---|
| 4,384,042 A | 5/1983 | Miike et al. |
| 4,916,058 A | 4/1990 | Aoyama et al. |
| 6,703,245 B2 * | 3/2004 | Sumitani et al. ............ 436/136 |
| 2003/0082823 A1 | 5/2003 | Sumitani et al. |

FOREIGN PATENT DOCUMENTS

| JP | 57-94052 | 6/1982 |
|---|---|---|
| JP | 60-33479 | 8/1985 |
| JP | 4-27839 | 5/1992 |
| JP | 2004-45365 | 2/2004 |

\* cited by examiner

*Primary Examiner*—Maureen M Wallenhorst
(74) *Attorney, Agent, or Firm*—Hamre, Schumann, Mueller & Larson, P.C.

(57) ABSTRACT

A liquid reagent in which a methylene blue compound color former is stably stored in a liquid state; and a method of stabilizing a methylene blue compound color former in a liquid state. A methylene blue compound color former is stabilized by causing it to coexist with either a quaternary ammonium compound having a $C_{12}$ or higher hydrocarbon chain or a salt thereof in a liquid medium. Examples of the methylene blue compound color former include 10-(carboxymethylaminocarbonyl)-3,7-bis(dimethylamino) phenothiazine.

6 Claims, No Drawings

LIQUID REAGENT OF COLOR FORMER AND METHOD OF STABILIZING THE SAME

TECHNICAL FIELD

The present invention relates to a liquid reagent of a methylene blue-based color former and a method of stabilizing the same.

BACKGROUND ART

As a substrate that develops color by being oxidized, a methylene blue-based color former such as, for example, 10-(carboxymethylaminocarbonyl)-3,7-bis(dimethylamino) phenothiazine has been known. Methylene blue that is a chromophore in the methylene blue-based color former hardly fades in color, thereby allowing highly sensitive detection to be performed, and thus it is expected that the methylene blue-based color former will be used in various analyses.

Such a color former can be used, for example, in the case of determining the amount of an oxidizing substance such as hydrogen peroxide generated using an oxidoreductase by causing a reaction between the color former and the oxidizing substance and then measuring the amount of a color developed by measuring an absorbance. When a color former is to be used in such an enzyme reaction, generally, a solution prepared by dissolving the color former in water is used as a liquid reagent.

However, a methylene blue-based color former as described above has presented a problem of being so unstable as to develop color spontaneously when in a solvent such as water. Because of this, the use of a color former that has been stored in a liquid state may cause an increase in background absorbance in a measurement of an absorbance, thus degrading the accuracy of the measurement. In particular, although it is advantageous that, as described above, methylene blue that is a chromophore in a methylene blue-based color former has a property of hardly fading in color and thus achieves high sensitivity, methylene blue has presented a problem that part of the chromophore (methylene blue) that has been freed by natural oxidation also hardly fades in color compared with other chromophores, thus exerting an influence that hardly can be avoided. For example, when stored in an aqueous solution state, 10-(carboxymethylaminocarbonyl)-3,7-bis (dimethylamino)phenothiazine develops enough color spontaneously to exert an influence on a measurement within about one day, and deteriorates to such an extent that it hardly can be used as a reagent for an analysis any more within about three days (see Patent Document 1 or U.S. Pat. No. 4,916,058 corresponding thereto).

In order to prevent such an influence of spontaneous color development, it is required to prepare a liquid reagent every time a measurement is performed. This, however, leads to a complicated operation and also to a cost increase.

Patent Document 1: JP 4(1992)-27839 B

DISCLOSURE OF INVENTION

Problem to be Solved by the Invention

With the foregoing in mind, it is an object of the present invention to provide a liquid reagent of a methylene blue-base color former that can be stored stably even in a liquid state and a method of stabilizing the color former in a solvent.

Means for Solving Problem

In order to achieve the above-described object, a liquid reagent according to the present invention contains a methylene blue-based color former, quaternary ammonium having hydrocarbon chains with a carbon number of 12 or higher or a salt thereof, and a liquid medium.

Furthermore, a method of stabilizing a liquid reagent containing a methylene blue-based color former according to the present invention includes allowing the color former and quaternary ammonium having hydrocarbon chains with a carbon number of 12 or higher or a salt thereof to be present together in a liquid medium.

EFFECTS OF THE INVENTION

As described above, in a liquid reagent containing a methylene blue-based color former, quaternary ammonium having hydrocarbon chains with a carbon number of 12 or higher or a salt thereof (hereinafter, also referred to collectively as "quaternary ammonium") also is allowed to be present, and thus spontaneous color development of the methylene blue-based color former can be suppressed, though the mechanism of the suppression is unknown. This enables the color former to be stored in a liquid state, and thus, for example, it is no longer necessary to prepare a liquid reagent of a color former every time a measurement is performed, thereby facilitating an operation such as a measurement and also achieving a cost reduction. Moreover, even in the case where the liquid reagent of a color former according to the present invention after having been stored is used as a color-developing reagent causing a color-developing reaction, an increase in background absorbance in a measurement of an absorbance is suppressed, and thus the accuracy of the measurement also can be improved.

DESCRIPTION OF THE INVENTION

As described above, the liquid reagent of a methylene blue-based color former according to the present invention contains at least a methylene blue-based color former and is characterized by containing quaternary ammonium having hydrocarbon chains with a carbon number of 12 or higher or a salt thereof, and a liquid medium.

In the above-described liquid reagent according to the present invention, the methylene blue-based color former is allowed to be present together with the quaternary ammonium, and thus spontaneous color development thereof is suppressed to achieve stabilization, thereby enabling the color former to be stored in a liquid state. The storage is performed at a temperature, for example, in a range of 0 to 40° C., preferably in a range of 0 to 25° C., and more preferably in a range of 0 to 10° C., though there is no particular limitation.

Specifically, in the case of storing a liquid reagent of a methylene blue-based color former at 10° C. without adding quaternary ammonium thereto, for example, with the methylene blue-based color former having a concentration of 0.05 mmol/L, after a storage period of 10 days, the absorbance measured at 658 nm as the absorption wavelength of methylene blue increases to, for example, 180 mAbs. On the other hand, even when stored at 10° C. and even after having been stored for at least 3 days, for example, 4, 5, 6, 7, 8, 9, 10 days, the liquid reagent according to the present invention allows spontaneous color development of the methylene blue-based color former to be prevented and/or suppressed and can be used adequately as a reagent of a color former for about 20 to 300 days.

The liquid reagent of a methylene blue-based color former according to the present invention is useful as, for example, a liquid reagent such as of a color-developing substrate in a redox reaction as described above, though there is no particular limitation on its applications.

In the present invention, a methylene blue-based color former refers to a methylene blue-based substrate that develops color by oxidation and specifically refers to a compound that frees methylene blue that is a chromophore by oxidation. Examples of such a compound include 10-(carboxymethylaminocarbonyl)-3,7-bis(dimethylamino)phenothiazine (hereinafter, referred to as "DA-67"), 10-(acetylaminocarbonyl)-3,7-bis (dimethylamino)phenothiazine, 10-(phenylcarbonyl)-3,7-bis(dimethylamino) phenothiazine (Compound No. 20 described in JP 4(1992)-27839 B), 10-(3-methylcarboxyamino)-hexamethyl-amino)-3,7-bis(dimethylamino) phenothiazine (Compound No. II-4 described in JP60(1985)-33479 B), 10-(((3-(methylcarboxyamino)-4-methyl)-phenyl)-amino)-3,7-bis (dimethylamino)phenothiazine (Compound No. II-5 in the aforementioned document), 10-((3-(methylcarboxyaminomethyl)-phenyl) -methylamino)-3,7-bis(dimethylamino)phenothiazine (Compound No. II-6 in the aforementioned document), 10-(1-naphthaleneamino)-3,7-bis(dimethyl amino)phenothiazine (Compound No. II-7 in the aforementioned document), 10-(methyl)-3,7-bis(dimethylamino)phenothiazine (Compound No. II-8 in the aforementioned document), 10-(phenylamino)-3,7-bis(dimethylamino) phenothiazine (Compound No. II-9 in the aforementioned document), and 10-(methylamino)-3,7-bis (dimethylamino)phenothiazine (Compound No. II-11 in the aforementioned document).

The carbon number of hydrocarbon chains of quaternary ammonium used in the present invention may be any number as long as the number is 12 or higher. The number is, for example, 13, 14, 15, 16, 17, 18, 19, or 20 and is preferably 14 or higher, 15 or higher, 16 or higher, 17 or higher, in a range of 14 to 18, in a range of 16 to 18, 17, or 18. In the present invention, the "carbon number of hydrocarbon chains of quaternary ammonium" preferably refers to the number of carbon atoms in a hydrocarbon group that is any one of four groups of quaternary ammonium.

Examples of the hydrocarbon group include a straight-chain or branched alkyl group, a cyclic alkyl group, a straight-chain or branched or cyclic alkyl group having a substituent, and an aryl group having a substituent. These substituents are identical to or different from each other and examples thereof include halogen, a straight-chain or branched alkyl group, a phenyl group, a hydroxyl group, and a straight-chain or branched $C_1$-$C_6$ alkoxy group. Examples of the aryl group include a phenyl group or a cyclohexyl group. Alternatively, aside from these groups, the aryl group may be a straight-chain or branched chain alkylcarbonyl group.

Specific examples of quaternary ammonium used in the present invention include benzethonium chloride, stearyltrimethylammonium chloride, cetyltrimethylammonium bromide, cetyltrimethylammonium chloride, hexadecyltrimethylammonium bromide, hexadecyltrimethylammonium chloride, benzalkonium chloride, benzyldimethyltetradecylammonium chloride, myristyltrimethylammonium bromide, myristyltrimethylammonium chloride, coconutamine acetate, and lauryltrimethylammonium chloride. These compounds may be used alone or in combination of two or more types. Further, as the quaternary ammonium, a mixture of quaternary ammoniums having hydrocarbon chains with varying carbon numbers also can be used as long as any one of the quaternary ammoniums satisfies the above-described ranges of a hydrocarbon number. Further, in the present invention, there is no particular limitation on the type of a salt in a quaternary ammonium salt.

The concentration of the color former in the liquid reagent according to the present invention is, for example, in a range of 1 to 10,000 µmol/L, and preferably in a range of 5 to 1,000 µmol/L. The concentration of the quaternary ammonium in the liquid reagent is, for example, in a range of 2 to 100,000 µmol/L, preferably in a range of 50 to 30,000 µmol/L, and particularly preferably in a range of 100 to 10,000 µmol/L. Though not particularly limited, the respective contents of the color former and the quaternary ammonium in the liquid reagent according to the present invention could be set so as to have required concentrations, respectively, when added to, for example, a sample, a reaction solution or the like.

In the liquid reagent according to the present invention, the addition ratio of the quaternary ammonium with respect to 0.1 mmol of the color former is, for example, in a range of 10 to 100,000 µmol, preferably in a range of 100 to 10,000 µmol, and more preferably 500 to 10,000 µmol.

Though not particularly limited, a liquid medium contained in the liquid reagent generally is an aqueous solvent such as, for example, water, or a buffer solution. As the buffer solution, buffer solutions in general use can be used and examples thereof include an ADA buffer solution, a Bis-Tris buffer solution, a PIPES buffer solution, a phosphate buffer solution, a MES buffer solution, a MOPS buffer solution, a citrate buffer solution, a HEPES buffer solution, a TAPS buffer solution, a glycylglycine buffer solution, a glycinamide buffer solution, and a Tris-HCl buffer solution. The concentration of the buffer solution is, for example, in a range of 1 to 500 mM and preferably in a range of 5 to 100 mM.

After being prepared, the liquid reagent according to the present invention has a pH, for example, in a range of pH 3 to 11 and preferably of pH 4.5 to 9, though there is no particular limitation.

Preferably, in the liquid reagent according to the present invention, at least one chelating agent selected from the group consisting of ethylene diaminetetraacetic acid (EDTA), diethylenetriaminepentaacetic acid (DTPA), trans-1,2-diaminocyclohexane-N,N,N',N'-tetraacetic acid (CyDTA), O,O'-bis(2-aminoethyl)ethyleneglycol-N,N,N',N'-tetraacetic acid (GEDTA), and nitrilotriacetic acid (NTA); sodium azide; or the like further is allowed to be present. By allowing these substances further to be present, spontaneous color development can be suppressed further. One or two or more types among these substances may be allowed to be present in the liquid reagent.

Furthermore, the liquid reagent according to the present invention suitably may contain, for example, an additive required for a redox reaction depending on the intended use of the liquid reagent.

Next, the stabilization method according to the present invention is a method of stabilizing a liquid reagent containing at least a methylene blue-based color former and is characterized by allowing the color former and quaternary ammonium as described above to be present together in a liquid medium as described above. Unless otherwise specified, the respective types, addition ratios and the like of the color former, the quaternary ammonium and a solvent are the same as described earlier. In the present invention, "stabilizing a liquid reagent of a color former" refers to a function or a state of maintaining suppression of self-color development of a methylene blue-based color former in a liquid medium, and encompasses, for example, "storing the color former in a liquid medium and/or the liquid reagent" and "preserving the color former in a liquid medium and/or the liquid reagent." The stabilization method according to the present invention makes it possible to stabilize, store, and/or preserve a methylene blue-based color former in a liquid reagent for at least 3 days, for example, 4, 5, 6, 7, 8, 9, 10, 11, 12, 13, 14 days or more, or about 20 to 300 days while preventing and/or suppressing spontaneous color development of the color former. Even after these days have elapsed, preferably, the liquid reagent according to the present invention can be used as a reagent causing a color-developing reaction.

The stabilization method according to the present invention can be performed by, for example, dissolving or suspending a methylene blue-based color former and quaternary ammonium as described above in a liquid medium as described above. A liquid thus prepared can be used as the liquid reagent according to the present invention.

In another aspect, the present invention provides a kit for performing the stabilization method according to the present invention, and the kit includes a methylene blue-based color former and quaternary ammonium as described above. Preferably, as required, the kit further includes a liquid medium as described above and/or an instruction manual. Preferably, the instruction manual explains, for example, that performing the stabilization method according to the present invention using the kit makes it possible to stabilize, store, and/or preserve the methylene blue-based color former for at least 3 days, for example, 4, 5, 6, 7, 8, 9, 10, 11, 12, 13, 14 days or more, or about 20 to 300 days while preventing and/or suppressing spontaneous color development, thereby allowing a reagent thus obtained to be used as a reagent causing a color-developing reaction.

In still another aspect, the present invention provides a kit for detection and/or measurement, and the kit includes a methylene blue-based color former, quaternary ammonium as described above, a reagent used for a reaction in which the methylene blue-based color former is allowed to develop color, and an instruction manual for performing the stabilization method according to the present invention. Preferably, as required, the kit further includes a liquid medium as described above. In this aspect, the "detection and/or measurement" is not particularly limited and encompasses, for example, detection and/or measurement of hydrogen peroxide or detection and/or measurement of a conventionally known chemical substance through the generation of hydrogen peroxide. In this aspect, the "reagent used for a reaction in which a methylene blue-based color former is allowed to develop color" is not particularly limited, and examples thereof include various types of peroxidases (POD). The reagent may further contain an oxidoreductase that reacts with a substrate to generate hydrogen peroxide such as, for example, oxidases of various types or a dehydrogenase, a protease that acts on a substrate, or the like. Therefore, specific examples in this aspect include a kit for detection/measurement of glycated protein that includes a methylene blue-based color former, quaternary ammonium as described above, POD, fructosyl amino acid oxidase (FAOD), and the instruction manual, and when required, further includes various types of proteases. Preferably, the instruction manual explains, for example, that performing the stabilization method according to the present invention using the kit in this aspect makes it possible to stabilize, store, and/or preserve the methylene blue-based color former for at least 3 days, for example, 4, 5, 6, 7, 8, 9, 10, 11, 12, 13, 14 days or more, or about 20 to 300 days while preventing and/or suppressing spontaneous color development, thereby allowing the kit to be used for detection and/or measurement.

EXAMPLE 1

The stability (change in absorbance) in the case where DA-67 and quaternary ammonium were allowed to be present together in a solvent was examined.

TABLE 1

| <First Reagent: R1-1> | |
|---|---|
| MOPS | 30 mmol/L(pH 7.5) |
| FAOD | 2.5 KU/L* |
| (trade name: FPOX-CE, produced by Kikkoman Corporation, used also in the following examples) | |
| POD | 2 KU/L* |
| <Second Reagent: R2-1> | |
| additive (listed in Table 2 below) | 1 g/L |
| methylene blue-based color-developing reagent | 0.25 mmol/L |
| (trade name: DA-67, produced by Wako Pure Chemical Industries, Ltd., used also in the following examples) | |
| metalloprotease | 2400 KU/L* |
| (produced by Arkray, Inc.) | |
| $CaCl_2$ | 5 mmol/L |
| MOPS | 30 mmol/L (pH 6.5) |

*KU: $10^3$ × U (enzyme unit)

<Measurement Method>

To 78 µL of the first reagent (R1-1) that has been stored at 4° C. for 12 days, 26 µL of the second reagent (R2-1) that has also been stored at 4° C. for 12 days was added, and a resultant mixture was incubated at 37° C. for 5 minutes. Then, an absorbance ($A_0$) at a wavelength of 658 nm in a reaction solution immediately before the addition of the second reagent thereto and an absorbance ($A_5$) at a wavelength of 658 nm in the reaction solution after 5 minutes from the addition of the second reagent thereto were measured with a biochemical automatic analyzer (trade name: JCA-BM8: produced by JEOL Ltd., used also in the following examples), and a difference ($A_5$-$A_0$) between them was determined. Table 2 below shows results of the determination.

TABLE 2

| | Additive | $A_5$-$A_0$ |
|---|---|---|
| Ex. 1 | benzethonium chloride | 0.026 |
| Com. Ex. 1-1 | not added | 0.117 |
| Com. Ex. 1-2 | D-(+)-trehalose | 0.095 |
| Com. Ex. 1-3 | glutaraldehyde | 0.083 |
| Com. Ex. 1-4 | collagen peptide | 0.099 |
| | trade name: Nippi Peptide PRA | |
| Com. Ex. 1-5 | pectin | 0.094 |
| Com. Ex. 1-6 | heparin sodium | 0.080 |
| Com. Ex. 1-7 | polyethylene glycol | 0.093 |
| | trade name: Polyethylene Glycol 6000 | |
| Com. Ex. 1-8 | trade name: Polyethylene Glycol 4000000 | 0.093 |
| Com. Ex. 1-9 | polypropylene glycol | 0.089 |
| | trade name: Triol type 1500 | |
| Com. Ex. 1-10 | polyethylene glycol | 0.113 |
| | trade name: Polyethylene Glycol #1000 | |
| Com. Ex. 1-11 | sodium alginate (300-400 cps) | 0.093 |
| Com. Ex. 1-12 | polyvinylpyrrolidone | 0.207 |
| | trade name: Polyvinylpyrrolidone 25 | |
| Com. Ex. 1-13 | trade name: Polyvinylpyrrolidone K-30 | 0.220 |
| Com. Ex. 1-14 | trade name: Polyvinylpyrrolidone K-90 | 0.197 |
| Com. Ex. 1-15 | propylene glycol alginate | 0.092 |
| Com. Ex. 1-16 | pullulan | 0.095 |
| | trade name: Pullulan PF-20 | |
| Com. Ex. 1-17 | hydroxypropyl cellulose | 0.102 |
| | trade name: HPC-SL | |
| Com. Ex. 1-18 | trade name: HPC TC-5E | 0.097 |
| Com. Ex. 1-19 | polyvinyl alcohol | 0.093 |
| | trade name: PVA103 | |

TABLE 2-continued

| | Additive | $A_5-A_0$ |
|---|---|---|
| Com. Ex. 1-20 | trade name: PVA210 | 0.097 |
| Com. Ex. 1-21 | trade name: PVA403 | 0.098 |
| Com. Ex. 1-22 | trade name: PVA105 | 0.093 |
| Com. Ex. 1-23 | trade name: PVA203 | 0.095 |
| Com. Ex. 1-24 | trade name: PVA205 | 0.092 |
| Com. Ex. 1-25 | carboxymethyl cellulose trade name: CMC1105 | 0.096 |
| Com. Ex. 1-26 | trade name: CMC1205 | 0.130 |
| Com. Ex. 1-27 | trade name: CMC1330 | 0.098 |

Unit: Abs.

As shown in Table 2 above, in a control example (Comparative Example 1-1), the storage for a period of 12 days led to the occurrence of spontaneous color development, resulting in an increase in absorbance. On the other hand, in Example 1, since DA-67 and the quaternary ammonium were allowed to be present together in the second reagent, an increase in absorbance could be suppressed to about one-fifth of that in the case of the control example (Comparative Example 1-1). Generally, a color former or the like exhibiting low stability possibly is allowed to be present together with a stabilizer such as a polymer, and in Comparative Examples 1-2 to 1-27, various types of polymers further were allowed to be present. A comparison with such cases of Comparative Examples 1-2 to 1-27 also shows that Example 1 remarkably could prevent an increase in absorbance. Based on these results, it can be said that by allowing a methylene blue-based color former such as DA-67 to be present together with quaternary ammonium, even when in a liquid state, the color former can be prevented from developing color spontaneously, thereby allowing an increase in background absorbance to be suppressed.

EXAMPLE 2

The stability (change in absorbance) in the case where DA-67 and each of various types of quaternary ammoniums were allowed to be present together in a solvent was examined.

TABLE 3

| <First Reagent: R1-2A> | |
|---|---|
| purified water | |
| <First Reagent: R1-2B> | |
| PIPES | 30 mmol/L (pH 7.5) |
| dodecyl maltoside | 3 g/L |

TABLE 3-continued

| FAOD | 2.5 KU/L* |
|---|---|
| POD | 2 KU/L* |
| <Second Reagent: R2-2> | |
| quaternary ammonium | 0.2 g/L or 1 g/L |
| DA-67 | 0.05 mmol/L |
| metalloprotease (produced by Arkray, Inc.) | 2400 KU/L* |
| $CaCl_2$ | 5 mmol/L |
| MOPS | 30 mmol/L (pH 6.5) |

<Quaternary Ammonium to be added to Second Reagent> stearyltrimethylammonium chloride (trade name: produced by Nacalai Tesque, Inc.)
cetyltrimethylammonium bromide
hexadecyltrimethylammonium bromide
benzalkonium chloride
benzyldimethyltetradecylammonium chloride
myristyltrimethylammonium bromide
coconutamine acetate (trade name: Acetamin 24: produced by Kao Corporation)
lauryltrimethylammonium chloride (trade name: Cortamine 24P: produced by Kao Corporation)
tetraethylammonium chloride
benziltriethylammonium bromide
benziltrimethylammonium bromide

*KU: $10^3$ × U (enzyme unit)

To 78 μL of the first reagent (R1-2A or R1-2B) that has been stored at 4° C. for 14 days, 26 μL of the second reagent (R2-2) that has also been stored at 4° C. for 14 days was added, and a resultant mixture was incubated at 37° C. for 5 minutes. Then, an absorbance ($A_0$) at a wavelength of 658 nm in a reaction solution immediately before the addition of the second reagent thereto and an absorbance ($A_5$) at a wavelength of 658 nm in the reaction solution after 5 minutes from the addition of the second reagent thereto were measured with a biochemical automatic analyzer (trade name: JCA-BM8: produced by JEOL Ltd., used also in the following example), and a difference ($A_5-A_0$) between them was determined. As a control example (Comparative Example 2-1), a sample was prepared in which purified water was used in place of quaternary ammonium in the second reagent (R2-2). Table 4 below shows results of the determination. Through the use of R1-2A (purified water) as the first reagent, it was confirmed that spontaneous color development of DA-67 contained in the second reagent was suppressed. Further, through the use of R1-2B (enzyme reagent), it was confirmed that also in the case where the present invention was applied to a glycated protein (HbA1c) measurement system, spontaneous color development of DA-67 was suppressed.

TABLE 4

| | | Absorbance First Reagent | | | |
|---|---|---|---|---|---|
| | | Purified Water (R1-2A) | | Enzyme Reagent (R1-2B) | |
| | | Concentration of Quaternary Ammonium | | | |
| Quaternary Ammonium to be added to Second Reagent | | 1.0 g/L | 0.2 g/L | 1.0 g/L | 0.2 g/L |
| Ex. 2-1 | stearyltrimethylammonium chloride | 0.004 | 0.004 | 0.007 | 0.007 |
| Ex. 2-2 | cetyltrimethylammonium bromide | 0.003 | 0.004 | 0.007 | 0.007 |
| Ex. 2-3 | hexadecyltrimethylammonium bromide | 0.004 | 0.004 | 0.008 | 0.007 |
| Ex. 2-4 | benzalkonium chloride | 0.003 | 0.004 | 0.007 | 0.010 |

TABLE 4-continued

| | | Absorbance First Reagent | | | |
|---|---|---|---|---|---|
| | | Purified Water (R1-2A) | | Enzyme Reagent (R1-2B) | |
| | | Concentration of Quaternary Ammonium | | | |
| | Quaternary Ammonium to be added to Second Reagent | 1.0 g/L | 0.2 g/L | 1.0 g/L | 0.2 g/L |
| Ex. 2-5 | benzyldimethyltetradecylammonium chloride | 0.003 | 0.004 | 0.007 | 0.009 |
| Ex. 2-6 | myristyltrimethylammonium bromide | 0.003 | 0.009 | 0.006 | 0.011 |
| Ex. 2-7 | coconutamine acetate | 0.006 | 0.007 | 0.009 | 0.010 |
| Ex. 2-8 | lauryltrimethylammonium chloride | 0.004 | 0.008 | 0.006 | 0.010 |
| Com. Ex. 2-1 | not added <control example> | 0.014 | | 0.015 | |
| Com. Ex. 2-2 | tetraethylammonium chloride | 0.012 | 0.014 | 0.014 | 0.016 |
| Com. Ex. 2-3 | benziltriethylammonium bromide | 0.013 | 0.013 | 0.015 | 0.015 |
| Com. Ex. 2-4 | benziltrimethylammonium bromide | 0.013 | 0.013 | 0.015 | 0.015 |

Unit: Abs

As shown in Table 4 above, it was found that according to Examples 2-1 to 2-8 using quaternary ammoniums having hydrocarbon chains with carbon numbers of 12 or higher, compared with the control example (Comparative Example 2-1) to which quaternary ammonium was not added and Comparative Examples 2-2 to 2-4 using quaternary ammoniums that did not satisfy the carbon numbers required as above, spontaneous color development during a storage period could be suppressed.

EXAMPLE 3

The stability (change in absorbance) in terms of the pH in the case where DA-67 and quaternary ammonium were allowed to be present together in a solvent was examined.

TABLE 5

| <First Reagent: R1-3> | |
|---|---|
| purified water | |
| <Second Reagent: R2-3A (Example 3)> | |
| hexadecyltrimethylammonium | 0.2 g/L |
| DA-67 | 0.05 mmol/L |
| buffer solution | 50 mmol/L |
| <Second Reagent: R2-3B (Comparative Example 3)> | |
| DA-67 | 0.25 mmol/L |
| buffer solution | 50 mmol/L |
| <Buffer Solution to be added to Second Reagent> | |
| citric acid - KOH | pH 4.6 |
| citric acid - KOH | pH 5.5 |
| MES - KOH | pH 5.5 |
| MES - KOH | pH 6.1 |
| MES - KOH | pH 7.0 |
| HEPES - KOH | pH 6.8 |
| HEPES - KOH | pH 7.4 |
| HEPES - KOH | pH 8.2 |
| TAPS - KOH | pH 7.7 |
| TAPS - KOH | pH 8.4 |
| TAPS - KOH | pH 9.1 |
| Imidazol - HCl | pH 6.3 |
| Imidazol - HCl | pH 7.0 |
| Imidazol - HCl | pH 7.7 |
| Tris - HCl | pH 7.0 |
| Tris - HCl | pH 8.0 |
| Tris - HCl | pH 9.0 |
| GlyAmid (glycinamide) | pH 7.5 |
| GlyAmid | pH 8.2 |
| GlyAmid | pH 9.0 |

<Measurement Method>

The second reagents (R2-3A, R2-3B) were stored at 5° C. for 2 days, respectively. Further, 78 μL of the first reagent (R1-3) and 13 μL of purified water were mixed together, and a resultant mixture was incubated at 37° C. for 5 minutes. To this mixture, 19.5 μL of each of the second reagents that have been stored was added, and a resultant mixture was incubated at 37° C. for 5 minutes so that a color-developing reaction was caused. Then, an absorbance ($A_0$) at a wavelength of 658 nm in a reaction solution immediately before the addition of the second reagent thereto and an absorbance ($A_5$) at a wavelength of 658 nm in the reaction solution after 5 minutes from the addition of the second reagent thereto were measured with a biochemical automatic analyzer (trade name: JCA-BM8), and a difference ($A_5$-$A_0$) between them was determined. Example 3 shows results obtained by the use of R2-3A as the second reagent, and Comparative Example 3 shows results obtained by the use of R2-3B as the second reagent. Differences between the results of Example 3 and the results of Comparative Example 3 also were determined. Table 6 below shows results of both the determinations.

TABLE 6

| Buffer Solution | pH | Ex. 3 (R2-3A) | Com. Ex. 3 (R2-3B) | Com. Ex. 3 – Ex. 3 |
|---|---|---|---|---|
| citric acid-KOH | pH 4.6 | 0.005 | 0.008 | 0.003 |
| citric acid-KOH | pH 5.5 | 0.004 | 0.010 | 0.005 |
| MES-KOH | pH 5.5 | 0.005 | 0.017 | 0.012 |
| MES-KOH | pH 6.1 | 0.005 | 0.014 | 0.009 |
| MES-KOH | pH 7.0 | 0.006 | 0.014 | 0.008 |
| HEPES-KOH | pH 6.8 | 0.008 | 0.012 | 0.003 |
| HEPES-KOH | pH 7.4 | 0.006 | 0.013 | 0.007 |
| HEPES-KOH | pH 8.2 | 0.006 | 0.018 | 0.012 |

TABLE 6-continued

| Buffer Solution | pH | Ex. 3 (R2-3A) | Com. Ex. 3 (R2-3B) | Com. Ex. 3 – Ex. 3 |
|---|---|---|---|---|
| TAPS-KOH | pH 7.7 | 0.006 | 0.017 | 0.011 |
| TAPS-KOH | pH 8.4 | 0.028 | 0.177 | 0.149 |
| TAPS-KOH | pH 9.1 | 0.030 | 0.234 | 0.205 |
| Imidazol-HCl | pH 6.3 | 0.046 | 0.328 | 0.282 |
| Imidazol-HCl | pH 7.0 | 0.033 | 0.210 | 0.177 |
| Imidazol-HCl | pH 7.7 | 0.017 | 0.208 | 0.191 |
| Tris-HCl | pH 7.0 | 0.007 | 0.025 | 0.018 |
| Tris-HCl | pH 8.0 | 0.005 | 0.021 | 0.016 |
| Tris-HCl | pH 9.0 | 0.004 | 0.011 | 0.006 |
| GlyAmid | pH 7.5 | 0.005 | 0.013 | 0.008 |
| GlyAmid | pH 8.2 | 0.004 | 0.013 | 0.009 |
| GlyAmid | pH 9.0 | 0.003 | 0.009 | 0.006 |

Unit: Abs

As shown in Table 6 above, it was found that according to Example 3 in which quaternary ammonium was added, compared with Comparative Example 3 to which quaternary ammonium was not added, also in the cases of using various types of buffer solutions whose pH values varied, spontaneous color development during a storage period could be suppressed.

INDUSTRIAL APPLICABILITY

As described in the foregoing discussion, according to the liquid reagent of a methylene blue-based color former of the present invention, the color former can be stored in a liquid state, and thus, for example, it is no longer necessary to prepare a liquid reagent every time a measurement is performed, thereby facilitating an operation such as a measurement and also achieving a cost reduction. Moreover, even in the case where the liquid reagent according to the present invention after having been stored is used as a reagent causing a color-developing reaction, an increase in background absorbance in a measurement of an absorbance is suppressed, and thus the accuracy of the measurement also can be improved.

The invention claimed is:

1. A liquid reagent, comprising:
    a methylene blue-based color former, the methylene blue-based color former is 10-(carboxymethylaminocarbonyl)-3,7-bis(dimethylamino)phenothiazine or 10-(acetylaminocarbonyl)-3,7-bis(dimethylamino) phenothiazine;
    a quaternary ammonium having hydrocarbon chains with a carbon number of 12 or higher or a salt of the quaternary ammonium; and
    a liquid medium.

2. The liquid reagent according to claim 1,
    wherein at least one of the hydrocarbon chains of the quaternary ammonium having hydrocarbon chains is a hydrocarbon group with a carbon number of 12 or higher.

3. The liquid reagent according to claim 2,
    wherein the carbon number is in a range of 14 to 18.

4. A method of stabilizing a liquid reagent containing a methylene blue-based color former, the methylene blue-based color former is 10-(carboxy methylaminocarbonyl)-3,7-bis(dimethylamino)phenothiazine or 10-(acetylaminocarbonyl)-3,7-bis(dimethylamino)phenothiazine, and a quaternary ammonium having hydrocarbon chains with a carbon number of 12 or higher or a salt of the quaternary ammonium, the method comprising: putting the color former and quaternary ammonium together in a liquid medium.

5. A kit for performing a method of stabilizing a liquid reagent containing a methylene blue-based color former as claimed in claim 4, comprising:
    a methylene blue-based color former, the methylene blue-based color former is 10-(carboxymethylaminocarbonyl)-3,7-bis(dimethylamino)phenothiazine or 10-(acetylaminocarbonyl)-3,7-bis(dimethylamino) phenothiazine; and
    a quaternary ammonium having hydrocarbon chains with a carbon number of 12 or higher or a salt of the quaternary ammonium, wherein the methylene blue-based color former and the quaternary ammonium are present together in a liquid medium.

6. A kit for detection and/or measurement, comprising:
    a methylene blue-based color former, the methylene blue-based color former is 10-(carboxymethylaminocarbonyl)-3,7-bis(dimethylamino)phenothiazine or 10-(acetylaminocarbonyl)-3,7-bis(dimethylamino) phenothiazine;
    a quaternary ammonium having hydrocarbon chains with a carbon number of 12 or higher or a salt of the quaternary ammonium;
    a reagent used for a reaction in which the methylene blue-based color former is allowed to develop color; and
    an instruction manual for performing a stabilization method as claimed in claim 4, wherein the methylene blue-based color former and the quaternary ammonium are present together in a liquid medium.

* * * * *